United States Patent [19]

Wedding

[11] Patent Number: 4,649,760
[45] Date of Patent: Mar. 17, 1987

[54] METHOD AND APPARATUS FOR CONTROLLING FLOW VOLUME THROUGH AN AEROSOL SAMPLER

[76] Inventor: James B. Wedding, 2128 Sandstone Dr., Ft. Collins, Colo. 80524

[21] Appl. No.: 724,982

[22] Filed: Apr. 18, 1985

[51] Int. Cl.[4] .................... G01N 1/22

[52] U.S. Cl. .................... 73/863.23; 73/861.64

[58] Field of Search .................... 73/863.23, 861.64

[56] References Cited

U.S. PATENT DOCUMENTS

| | | | |
|---|---|---|---|
| 1,850,030 | 3/1932 | Pardoe | 73/861.64 |
| 3,817,100 | 6/1974 | Anderson et al. | 73/863.23 |
| 4,067,705 | 1/1978 | Karz | 55/210 |
| 4,246,788 | 1/1981 | Olin et al. | 73/863.23 X |
| 4,461,183 | 7/1984 | Wedding | 73/863.21 |

*Primary Examiner*—Jerry W. Myracle

*Attorney, Agent, or Firm*—James R. Young

[57] ABSTRACT

A volume flow control device for an aerosol sampler is disclosed. The device includes a mechanism for drawing the aerosol through the sampler. A critical flow venturi is disposed downstream in the sampler for maintaining a predetermined volume flow of aerosol through the sampler. The aerosol drawing mechanism is adapted to create a vacuum downstream of the venturi.

38 Claims, 5 Drawing Figures

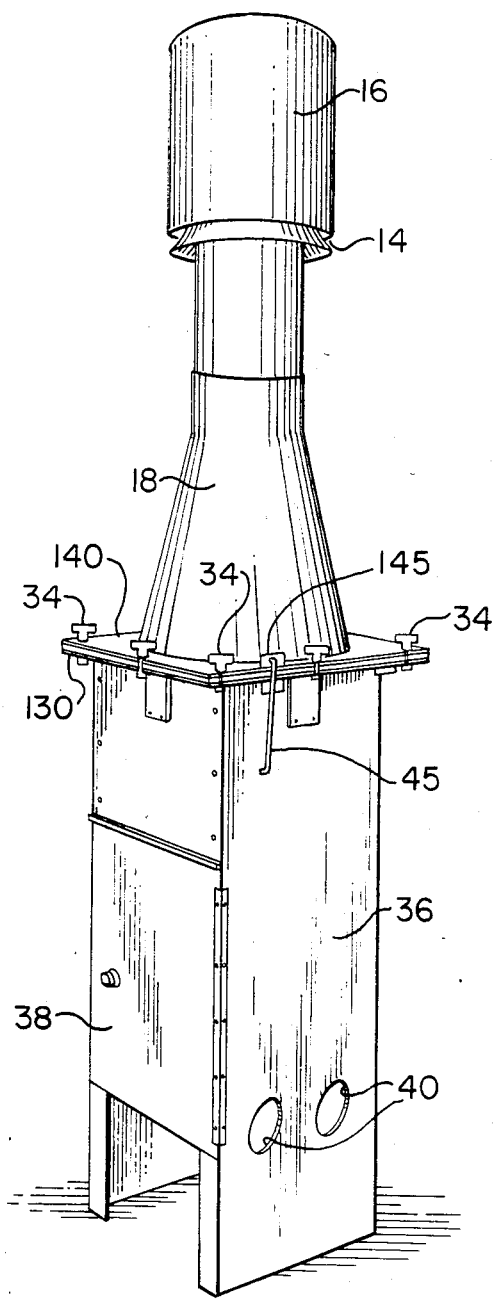
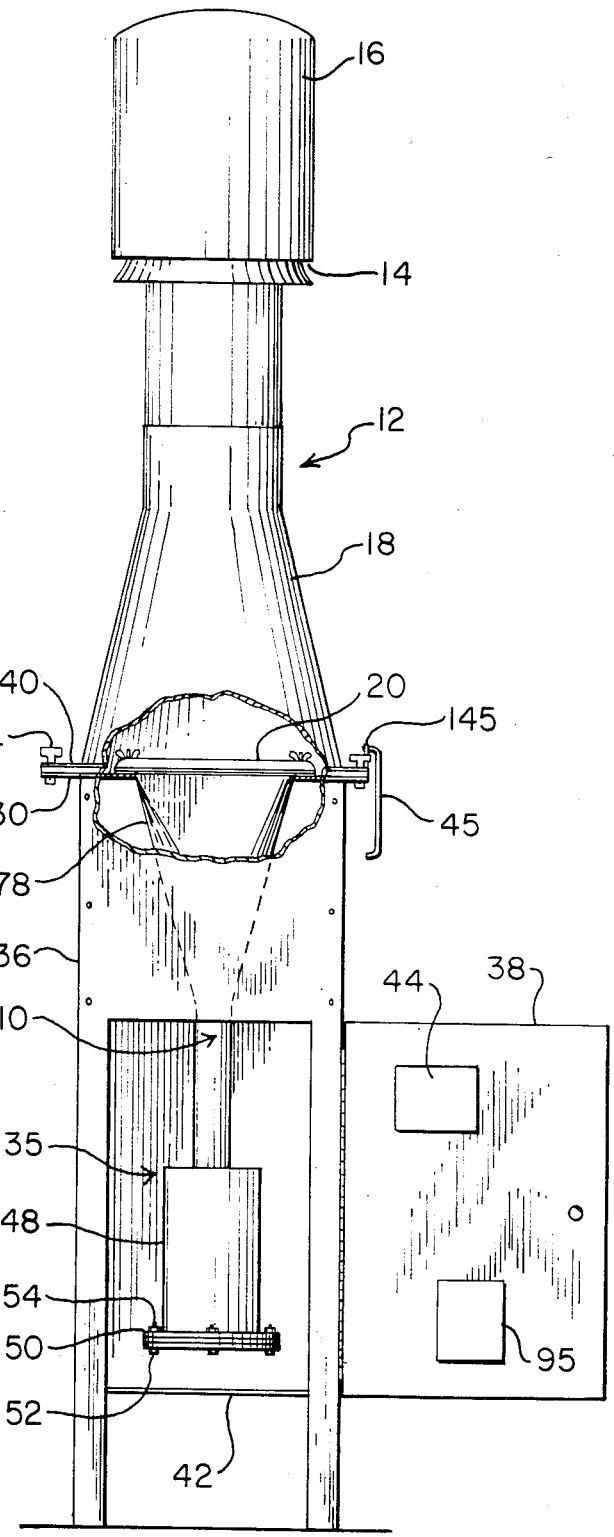
Fig. 1.
Fig. 2.

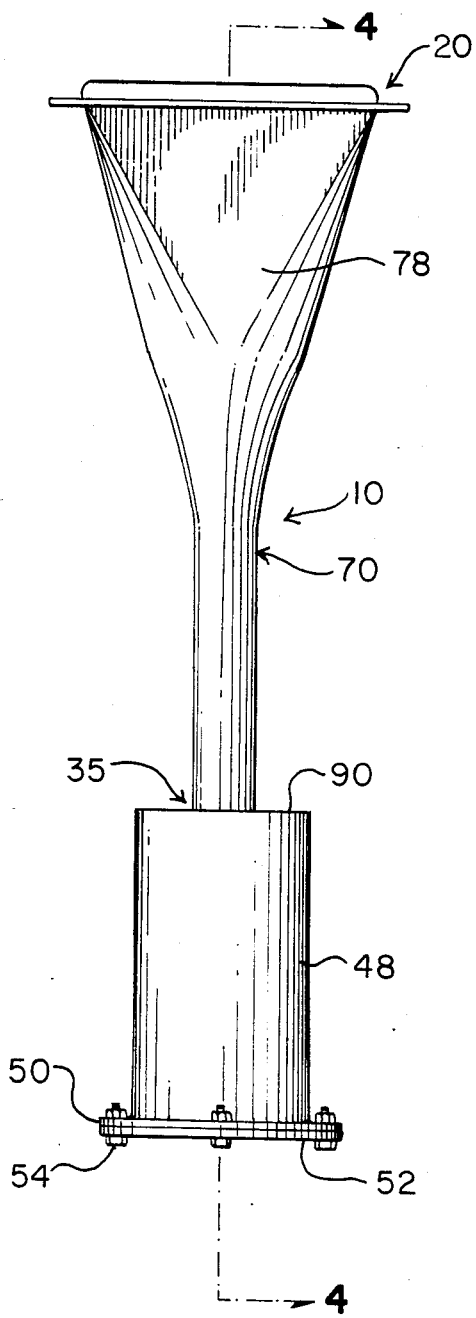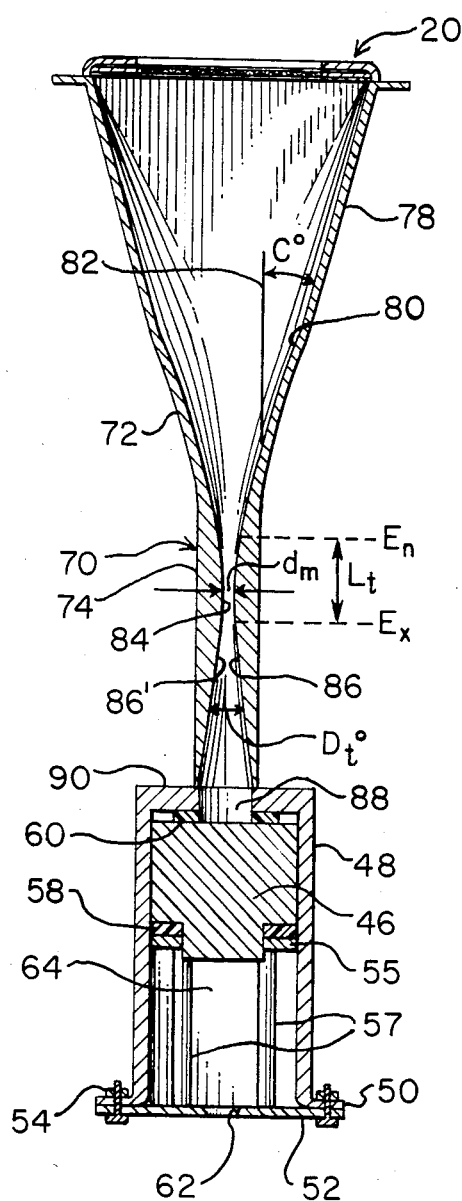
Fig. 3.
Fig. 4.

METHOD AND APPARATUS FOR CONTROLLING FLOW VOLUME THROUGH AN AEROSOL SAMPLER

BACKGROUND OF THE INVENTION

1. Field of the Invention

The present invention relates generally to aerosol sampling methods and devices and, more particularly, to high volume devices for sampling concentrations of particulate matter in ambient air. Specifically, the present invention relates to a method and apparatus for controlling flow volume and maintaining a constant mass and volumetric flow through such aerosol sampling devices.

2. Description of the Prior Art

It is recognized and generally accepted that gaseous air pollutants are deleterious to the health of persons. Scientists are also aware that particulate pollution in air has serious adverse health effects. The U.S. Environmental Protection Agency (EPA) has set standards for particulate matter in air in terms of mass per unit volume limits over a preselected period of time. For example, present standards for particulate matter are 75 micrograms per cubic meter average annual limit (geometric mean) and 260 micrograms per cubic meter in 24 hours (geometric mean) for particles up to a normal size range of 25 to 45 microns.

New data has become available which indicates that protection of public health may be better served by considering only those particles which are inhalable. The health risks posed by inhaled particles are influenced both by penetration and deposition of particles in various regions of the respiratory tract and by biological responses to these deposited materials. More specifically, it has been found that the risks of adverse health effects associated with deposition of ambient fine and coarse particles in the thorax (tracheobronchial and alveolar regions of the respirtatory tract) are markedly greater than for deposition in the extrathoracic (head) region. Maximum particle penetration to the thoracic region occurs during oronasal or mouth breathing. Further, it has been found that the risks of adverse health effects from extrathoracic deposition of general ambient particulate matter are sufficiently low that particles depositing only in that region can safely be excluded from the standard indicator. Consequently, the size-specific indicator for primary standards should represent those particles capable of penetrating to the thoracic region, including both the tracheobronchial and alveolar regions. As a result, the International Standards Organization has proposed a standard based upon particles deposited on the tracheobronchial regions of the human respiratory tract. This proposal is now referred to as the thoracic deposition TPC (Thoracic Particles).

The Clear Air Scientific Advisory Committee (CASAC) has now recommended to the United States Environmental Protection Agency (EPA) that a 10 micron particle size range be used as the new primary standard for average annual limits and 24 hour limits of micrograms per cubic meter clean air standards. Therefore, in accordance with sections 108 and 109 of the Clean Air Act, the EPA has reviewed and revised the criteria upon which primary and secondary particulate matter standards are based. The existing primary standards for particulate matter (measured as "total suspended particulate matter" or "TSP") have been 260 $\mu g/m^3$, averaged over a period of 24 hours and not to be exceeded more than once per year, and 75 $\mu g/m^3$ annual geometric mean. The secondary standard (also measured as TSP) has been 150 $\mu g/m^3$, averaged over a period of 24 hours, and not to be exceeded more than once per year.

As a result of its review and revision of the health and welfare criteria, the EPA has now proposed several revisions to its particulate matter standards. First, the EPA proposes that TSP as an indicator for particulate matter be replaced for both of the primary standards by a new indicator that includes only those particles with an aerodynamic diameter smaller than or equal to a nominal 10 micrometers ($PM_{10}$). Second, the EPA proposes that the level of the 24 hour primary standard be changed to a value to be selected from a range of 150 to 250 $\mu g/m^3$ and that the current deterministic form of the standard be replaced with a statistical form that permits one expected excess over the standard level per year. Third, the EPA proposes that the level and form of the annual primary standard be changed to a value to be selected from a range of 50 to 65 $\mu g/m^3$, expressed as an expected annual arithmetic mean. Fourth, the EPA now proposes that the current 24 hour secondary TSP standard be replaced by an annual TSP standard selected from a range of 70 to 90 $\mu g/m^3$, expected annual arithmetic mean.

As a consequence of these changes, a need exists to develop monitoring instruments that mimic the deposition of particles in the thoracic region of the human respiratory system. High volume sampling techniques to determine the amount of particulate matter within gases such as air are well known. 40 CPR Part 50, Appendix B, as amended by the EPA in the Federal Register, Volume 47, No. 234, Dec. 6, 1982, discloses reference methods and monitors for determining total suspended particulates in the atmosphere. The high volume sampler method disclosed therein is adapted to collect large samples to enable sufficient matter to be collected for analysis on a 4-place balance, and this technique has found wide acceptance in the industry.

However, the reproducibility and accuracy of particle concentration determined with such a high volume sampler has often been overlooked. In prior art high volume sampler devices, the blower motors used to draw the aerosol into the samplers generally have characteristic flow rate performance curves which show progressive decreases in the flow rates through the filters of the samplers as a result of increasing particulate accumulation on the filters. Thus, the flow rate in such a prior art device is not constant or known during the sampling period. Other variations in the flow rate of sampling can occur due to line voltage variations in the electrical circuits leading to the motor, temperature and pressure changes of the ambient air which significantly alter the pumping rate of the high volume sampler motor, and motor/blower performance degradation.

The EPA has now recognized that significant errors in the air volume determination can result from errors in flow rate and/or sampling time measurements. Therefore, the proposed rules promulgated by the EPA on Mar. 20, 1984, in 40 CFR Part 50 would require ambient aerosol samplers used to monitor compliance with the EPA clean air standards to be equipped with an automatic flow control device capable of maintaining the sample flow rate within certain specified limits.

Attempts have been made to regulate such high volume sampler devices to maintain constant air flow, which would require flow controllers that are capable of maintaining a flow rate independent of filter loading, temperature and pressure changes, as well as line voltage variations. Such a flow controller, of course, would improve the accuracy, representativeness and reproducibility of the measurements. However, the prior attempts to provide such flow controllers have not been very effective or successful. The devices which have been utilized in the past have suffered from a number of deficiencies, which include, among other things, the use of precision mechanical systems based on maintenance of a constant back pressure across an aperture, pressure tap or a capillary tube. All of these devices have been temperature sensitive and therefore require temperature-regulated enclosures or complicated temperature compensating devices for proper operation, none of which are completely satisfactory for long term, reliable, maintenance free use.

Some of the prior devices have also used the discharge pressure of the motor/blower as a measure of flow rate. While this kind of approach is apparently an attempt to a straightforward solution, such a system introduces another error. As the speed of the blower motor is increased to compensate for filter loading by particulate matter accumulating thereon, an increasingly heavy load is placed on the motor. As the motor thus becomes more and more heavily loaded, heat is generated which increases the temperature, and therefore the pressure, of the exhaust air. Thus, the discharge pressure of the blower motor is increased, which causes the control system to change the rate at which the motor operates. This resulting change is not in response to a change in the condition of the ambient air, but is instead a change caused by the heat of the blower motor. Consequently, this resulting changed speed of the blower motor causes an error in the control of the air flow through the sampler device.

Other attempts have been made to regulate the mass flow rate through such aerosol sampler devices. One specific device is the Kurz flow controller disclosed in U.S. Pat. No. 4,067,705. Laboratory studies have confirmed that this device is a constant mass controller and, when operating correctly, it will control the flow rate at a constant mass. However, such correct operation only occurs at a set point reference condition such as the 25° C. set point conditions specified by the EPA for calibration. It does not occur at normal ambient operating conditions encountered in the field. This limitation poses a distinct problem due to the fact that the above described amendments to 40 CFR Part 50 proceed on the assumption that flow controllers will yield constant flow at actual ambient operating conditions, not merely at reference conditions. It has been demonstrated that errors in actual volumetric flow rate of 25% to 30% can result if the flow controller is operated at actual ambient temperatures differing from the reference setpoint temperature, due to both diurnal and seasonal temperature variations. Thus, the value for total volume of air sampled used in calculating ambient particulate concentration levels will bear little resemblance to the actual volumes sampled. Also, the performance of particle size-specific inlets will not experience their designed linear flow rate, and sampler cutpoints for particle size could be adversely affected so as to not meet the EPA proposed regulations discussed above.

SUMMARY OF THE INVENTION

Accordingly, it is a general object of the present invention to provide an improved ambient aerosol sampler wherein the measurements obtained thereby are independent of filter loading, ambient aerosol temperature and pressure conditions, ambient wind velocity, and linear line voltage variations.

It is a more specific object of the present invention to provide a volume flow control method and device for an aerosol sampler wherein the volume flow through the sampler device is maintained at a constant predetermined flow level independent of filter loading and external ambient conditions.

Still another object of the present invention is to provide a volume flow control method and device for an aerosol sampler wherein minimal vacuum is required to draw the aerosol through the device at a constant flow rate.

To achieve the foregoing and other objects and in accordance with the purpose of the present invention, a volume flow control device is disclosed for an aerosol sampler. The flow control device includes a mechanism for drawing the aerosol through the sampler. A venturi is disposed downstream in the sampler for maintaining a predetermined volume flow of aerosol through the sampler. Finally, the aerosol drawing mechanism is adapted to create a vacuum downstream of the venturi independent of particle accumulation within the aerosol sampler. The method of the present invention includes the steps of positioning a critical flow venturi in the air flow path and drawing a sufficient vacuum through the venturi to maintain the mass flow of air therethrough at the maximum rate allowed by the venturi, thus maintaining constant volumetric flow through the sampler within normal ranges of ambient pressure and temperature (−30° C. to 50° C.). The method includes forming and using a venturi sized and dimensioned such that the critical or maximum rate of flow allowed therethrough corresponds to the desired constant air flow through the aerosol sampler.

BRIEF DESCRIPTION OF THE DRAWINGS

The features of the present invention which are believed to be novel are set forth with particularity in the appended claims. The invention, together with further objects and advantages thereof, may be best understood by reference to the following description taken in conjunction with the accompanying drawings and in which:

FIG. 1 is a perspective view of an ambient aerosol sampling device with housing assembly and incorporating a volume flow control mechanism of the present invention;

FIG. 2 is a front elevation view, with some parts broken away, of the device illustrated in FIG. 1 with the panel door open to reveal internal parts thereof;

FIG. 3 is an elevation view of the volume flow controller of FIG. 1 in a fully assembled relationship;

FIG. 4 is a cross-sectional view taken substantially along lines 4—4 of FIG. 3; and FIG. 5 is an exploded, perspective view of a volume flow controller constructed in accordance with the present invention and further illustrating filter media for use in an ambient aerosol sampler.

DETAILED DESCRIPTION OF THE PREFERRED EMBODIMENT

Figure 5:
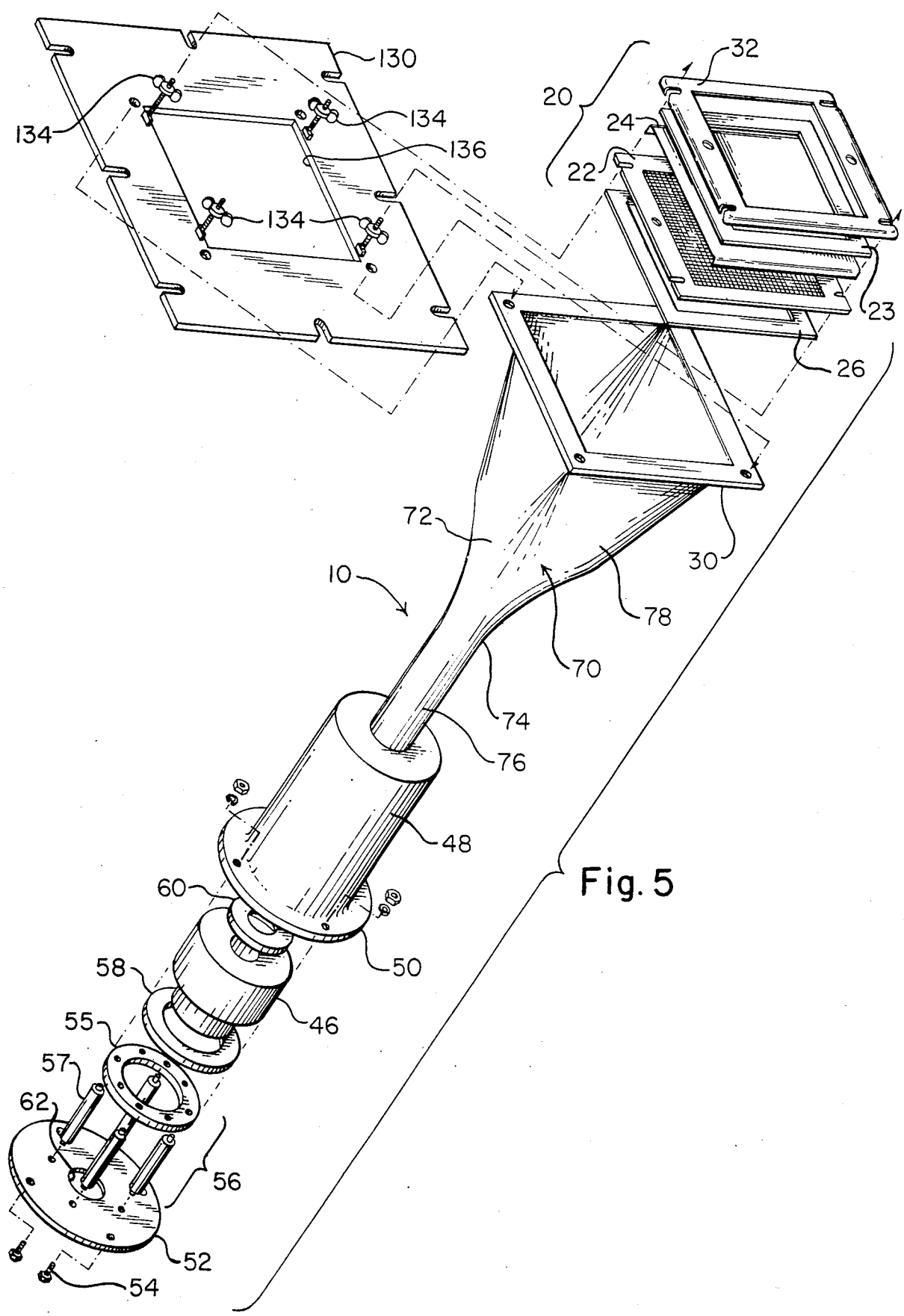

An aerosol sampler apparatus 12, which utilizes a flow controller device 10 according to the present invention, is shown in FIGS. 1 and 2. The aerosol sampler apparatus 12 generally includes an aerosol inlet/particle separator device 16. A detailed example of such ambient aerosol sampler inlet device is disclosed in my U.S. Pat. No. 4,461,183, the contents of which are specifically incorporated herein by reference. The purpose of the sampler inlet/separator 16 is to separate and remove larger particulate material entering the sampler at 14 from the remaining aerosol. The inlet 16 is usually designed to remove particles 10 microns and above. The remaining aerosol containing the finer particles of less than 10 microns is then directed through a flow transition duct 18 to a filter assembly 20.

The filter assembly 20 is of conventional design and is generally rectangular in shape. In preferred form, as illustrated in FIG. 5, the filter assembly 20 includes a support screen 22 which is covered by a removable filter element 24. Gaskets 26, 28 are provided for sealing the screen 22 and the filter 24 between a mounting plate 130 and a retainer member 32. The plate 130 is a part of the cabinet 36 and supports the flow transition duct 18 as well as the filter assembly 20. A plurality of attachment bolts 134 are pivotally mounted on the plate 130 and are utilized to assemble the filter assembly 20 and mount it to the plate 130. As is clearly illustrated in FIG. 5, the filter assembly 20 is adapted to permit easy removal of the screen 22 and the filter element 24 to enable measurement of the total accumulated particulate material collected thereon.

As previously mentioned, a principal function of this invention is to provide a predetermined constant volumetric flow of air through the filter assembly 20 independent of, and unaffected by, the accumulation of particulate matter on the filter element 24, as well as independent of the ambient air temperature, pressure, and wind conditions. To achieve this constant volumetric flow of air, the flow controller 10 is disposed preferably downstream of the filter assembly 20, although it can be disposed upstream of the filter assembly 20 if desired.

Once the remaining aerosol has been directed through the filter assembly 20 and the particulate aerosol material thereof captured and deposited on the filter 24, the remaining filtered air is directed through the opening 136 in plate 130 and into the flow controller 10 of the device 12. This flow controller 10 is preferably contained within a cabinet 36, which has a hinged door 38 to permit ready access to the flow controller 10. Once the filtered air has passed through the flow controller 10, it is exhausted through vents 40 disposed within the side wall of the cabinet 36. Preferably, a floor or baffle plate 42 is provided to direct the exhaust air through the vents 40 in lieu of churning up and aerosolizing dust and debris from the ground beneath the cabinet 36.

In accordance with the aforementioned EPA regulations and standard procedures, the device 12 is generally operated continuously for a predetermined standard time period, usually in the range of 12 to 24 hours, during which time particulate material is deposited on the filter element 24. After each 12 to 24 hour running period, the filter assembly 20 is disassembled and the loaded filter element 24 is carefully removed therefrom and replaced with a clean filter element. The loaded filter element 24 is then taken to a laboratory for careful weighing and measurement of the particlates collected thereon.

Typically, sampling is done every third day. To permit easy operation of the device 12, a timer 95 may be included within the cabinet 36 to automatically turn the device 12 on and off at predetermined intervals as described above.

In order to facilitate easy access to the filter assembly 20, the flow transition duct is mounted on a plate 140, as shown in FIGS. 1 and 2. The plate 140 is hinged to plate 130 and retained in a closed position by fasteners 34. An ear 145 on plate 140 cooperates with retainer 45 fastened to cabinet 36 to hold the plate 140 in an open position when the fasteners 34 are loosened or removed.

The flow controller 10 of the device 12 includes a critical flow venturi 70 and a blower motor 46 disposed within a motor housing 48 at the bottom of the flow controller 10. The motor 46 is adapted for drawing ambient aerosol into the sampler inlet 16 and through the device 12. Any blower motor 46 of conventional design may be utilized with the present invention so long as it is capable of achieving the functions described below.

The housing 48 preferably includes a flange 50 adapted to be secured to an end plate 52 by connecting members 54. The motor 46 is maintained within the housing 48 by a support assembly 56 comprised of a retainer ring 55 and struts 57. The struts 57 are anchored in the end plate 50 and bear on the retainer ring 55 to hold the motor 46 against the top 90 of motor housing 48. Gasket members 58, 60 are provided to seal the air flow into and out of the motor 46 and to cushion the motor mounting in the housing 48. An orifice 62 is provided in the central portion of the end plate 52 to permit the exhaust gas to pass therethrough into the cabinet 36 and out through the vents 40. Open space 64 is provided within the housing 48 under the motor 46 so that the quasi-static pressure created by the motor 46 can be monitored therein.

The venturi 70 includes a funnel section 78, a converging inlet portion 72 having a circular cross-section, a throat portion 74, and a diverging outlet portion 76. The funnel member 78 converges in form and converts the cross-sectional shape of the device 12 from the substantially rectangular configuration of the filter assembly 20 to a substantially circular cross-section in the converging inlet portion 72.

The interior of the converging inlet portion 72 is substantially in the form of a frustum of a cone leading to the interior 84 of the throat portion 74, or, as shown in FIG. 4, may have interior sidewalls with a slight inwardly convex curvature. As particularly illustrated in FIG. 4, an angle of convergence, C°, which is defined as the angle which one side portion 80 makes with the axis 82 of the venturi 70, is preferably in the range of 10° to 20°.

The throat portion 84 is defined from its entrance point, $E_n$, to its exit point, $E_x$. The throat 84 can have a length designated as $L_t$ and has an inner surface shaped somewhat like an hour glass so as to have an internal radius of curvature. This curvature creates a minimum throat diameter, $d_m$, at the approximate center of the throat portion 84. In the preferred illustrated embodiment, the minimum diameter of the throat portion, $d_m$, is defined by the relationship $10 \leq (Q_o/d_m) < 100$, where $Q_o$ is flow rate in c.f.m. and $d_m$ is minimum throat diameter in inches. The radius of curvature of the interior surface of throat 84 is approximately 5 inches. The throat diameter is in the range of 0.4 to 0.5 inches in the illustrated embodiment, and, as also illustrated in FIG. 4, the throat diameter is about one-twelfth the diameter of the entrance portion of the frustoconical inlet portion 72. Also, as illustrated in FIG. 4, the diameter of the throat 84 is about one-sixteenth the width of the rectangular filter and about one-twenty-fourth the width of the entrance to the funnel section 78. Therefore, the contraction ratio of the venturi 70 from the entrance of the converging inlet portion 72 to the smallest section of the throat 84 is over 50 to 1, and the contraction ratio of the venturi from the filter assembly 20 to the smallest section of the throat 84 is over 200 to 1, where the contraction ratio is the ratio of the cross-sectional area of the entrance to the cross-sectional area of the throat.

Moreover, the length of the throat portion 84, $L_t$, is approximately 2.2 inches. While the actual dimensions of the throat portion 84 will vary depending on the size of the device 10 and the consequent size of the venturi 70 necessary to service the device 10, the relationship between various portions of the throat portion 84 will not vary significantly. In order to achieve the desired critical venturi effect, the relationship between the length and minimum diameter of the throat portion 84 is such that the ratio of $L_t/d_m$ should be in the range of about 1 to 8 and is preferably approximately 5. Likewise, the radius of curvature of the inner surface 84 of the throat portion 74 should be in the range of 5 to 20 times $d_m$.

Downstream of the exit $E_x$ of the throat portion 84 is a divergent outlet portion 86 which functions as a divergent nozzle. A significant feature of the present invention is the angle which the inner surface 86 of the diverging portion 76 makes relative to the axis 82 of the venturi 70. As illustrated in FIG. 5, the total angle of divergence between opposite sides 86 and 86' of a cross-section of the diverging portion 76, such angle being illustrated by the designator $D_t°$, is preferably about 10°. This can also be expressed as a partial angle of divergence between the surface 86 and the axis 82 preferably of about 5°. If these angles are significantly greater, then the boundary layer of the air passing through the diverging portion 76 will separate and detach from the surface 86, 86'. The avoidance of separated flow along the surface 86, 86' is necessary in order to create the maximum choking or critical mass flow rate through the venturi 70. The fluid dynamics are such that a stable shock wave can be created and maintained within the throat portion 74 when the boundary layer remains attached to the interior surface 86, 86' of the divering portion upon exit from the throat portion 84.

Such a shock wave, when created, limits the mass flow of air through the venturi 10 to an absolute maximum, regardless of whether or how much the vacuum pulled by the blower motor 46 is increased. The shock wave is created when the mass flow rate of air through the venturi 10 reaches a critical rate. For purposes of this invention, the definition of the critical rate implicitly requires that the reference velocity is such that the Mach Number is unity. This condition in a fixed geometry realizes maximum flow per unit area, which is then a function only of the ratio $$\frac{P_o}{\sqrt{T_o}}.$$

This maximum in the curve of the mass flow per unit area is connected with the effect herein referenced as choking. For a given area condition, there is in subsonic flow a maximum initial Mach Number which can be maintained steadily and the flow is choked. This condition means that any change in exit condition, such as blower motor speed or exit pressure, does not affect the throat conditions and that $$\frac{W\sqrt{T_o}}{A_E P_o} \neq f(P_B/P_o)$$

where W is mass flow rate, $T_o$ is ambient temperature, $A_E$ is exit area, $P_o$ is stagnation pressure upstream of the filter which can be assumed to be ambient pressure, and $P_B$ is the stagnation or quasi-stagnation pressure in the blower motor. Thus, once this critical mass flow rate W is achieved and maintained, the resulting shock wave in the throat 84 regulates the air flow therethrough at an exact, unchangeable rate, regardless of ambient conditions of pressure and temperature within normal ranges of variation, for example from $-30°$ C. to $50°$ C.

Unless the boundary layer as described above is formed, a stable shock wave that remains within the throat portion 84 cannot be maintained. A sufficient ratio between $L_t/d_m$ is preferred to permit a stable shock wave to be formed and maintained within the throat portion 84.

Once the air flow passes through the diverging portion 86 of the venturi 70, it enters through an orifice 88 located in the upper surface 90 of the blower housing 48. The dimensions of the orifice 88 are not critical to the invention and are generally designed to match the inner diameter of the opening to the blower motor 46, which in the illustrated embodiment, is about 1.75 inches.

The blower motor 46 is designed to draw the initial aerosol into the device 12, through the filter assembly 20, and then through the venturi 70. This aerosol flow is achieved by creating a vacuum within the blower motor 46. Any blower motor that is capable of creating the required vacuum and moving the required air volume is satisfactory and many of such blower motors are generally available, and well-known to persons skilled in the art. Therefore, the specific structure of the blower motor 46 is not particularly important for the purposes of describing this invention other than to generally describe its location and functional interrelationship to other components of this invention.

Due to the relative dimensions and ratios of the venturi 70 as provided above, a critical or choking mass flow rate can be achieved and sustained within the venturi 70 by creating a fairly minimal vacuum within the orifice 88. In the illustrated embodiment, the pressure drop from the inlet 14 to the discharge 88 necessary to achieve the critial flow rate through the venturi 70 is approximately 20 inches of water. Of course, the actual pressure drop at any time depends on the particulate loading on filter element 24. Once the critical or choking mass flow rate is achieved within the venturi 70, the desired volume flow through the filter assembly 20 is created and maintained without variation.

The actual constant volume flow through the filter assembly 20 may be varied by changing critical venturi dimensions to the design parameters of the desired device 10. A standard accepted flow rate parameter is approximately 40 c.f.m., although the present invention is designed to be able to provide any desired constant volume flow rate of between 0.5 to 50 c.f.m.

As the amount of particulate matter accumulates on the filter member 24, there was a tendency in prior art devices for the flow rate through the filter assembly 20 to be reduced. However, given the nature of the critical flow venturi 70 of the present invention, if the critical or choking mass flow rate is maintained through the venturi 70, then a constant volume flow upstream of the venturi 70 through the filter assembly 20 will also be maintained. Moreover, the flow through the venturi 70 is not affected by and is maintained at the same level regardless of ambient pressure, temperature, or wind changes.

The actual choked mass flow rate $W_a^*$ through the choked flow venturi 70 is represented by equation (1):

$$W_a^* = C_f W^* \qquad (1)$$

where $C_f$ is the venturi flow coefficient and $W^*$ is the ideal choking mass flow rate in slugs/s. $C_f$ is determined empiracally by routine experiments well-known to the art and is generally in the range of $1.0 \pm 0.1$. For the embodiment illustrated in the figures and described specifically above, $C_f$ is about 0.997.

The ideal choking mass flow rate, $W^*$, can be calculated from equation (2):

$$W = \frac{CP_1 A^*}{\left[\frac{R}{M_W} T_1\right]^{\frac{1}{2}}} \qquad (2)$$

where:
C = a constant which, for air, is 0.6847
$P_1$ = stagnation pressure downstream of the filter assembly 20
$A^*$ = cross-sectional throat area where the flow is choked and is generally at $A_t$ which is in the area of the throat $E_n$ to $E_x$
R = a universal gas constant for air
$M_W$ = molecular weight of the gas, which in the present embodiment is air
$T_1$ = the temperature downstream of the filter 20

Through use of the above equations (1) and (2), the actual choked mass flow rate through the venturi 70 can be readily determined.

Another relationship which permits one to determine venturi 70 requirements based on the desired flow rate through the filter assembly 20 is defined by equation (3):

$$Q_o = C_f A_t \left[ C \frac{R}{M_W} \tfrac{1}{2} \right] \left[ 1 - \frac{P_f}{P_o} \right] [T_o \tfrac{1}{2}] \qquad (3)$$

For equation (3) the term $Q_o$ represents the volumetric flow rate through the filter assembly 20 based on atmospheric conditions. The additional terms utilized in equation (3) not previously discussed include the following:

$A_t$ = the throat area at $E_n$ $\Delta P_f$ = stagnation pressure loss across the filter 24, which is a function of filter loading
$P_o$ = stagnation pressure above the filter 24, which is assumed to be ambient temperature
$T_o$ = ambient temperature Given equations (1), (2), and (3) as well as the dimensional ratios for the venturi 70 described above, a volume flow control mechanism can be readily designed for any desired flow rate sampler which will maintain a constant flow volume through the filtering media of the aerosol sampler. This can be achieved by using the above device and method regardless of the accumulation of particulate matter within the filter media and despite changes in ambient temperature and pressure, whether such changes be daily fluctuations or seasonal in nature.

The design of the venturi is such that the mere creation of a small vacuum downstream of the venturi configuration as described above permits a critical mass flow rate to be readily achieved and maintained within the venturi, which will in turn permit the continued maintenance of a predetermined constant volume flow through the filtering media of the aerosol sampler. It is appropriate to mention that while one of the benfits of this invention is that it can operate effectively with relatively low vacuum requirements, the principle of this invention is equally applicable to systems that utilize or require larger vacuums as well.

Since sensitive measuring devices, such as required on prior art sampling mechanisms, are not necessary with the present invention, the flow control mechanism of the present invention will also last substantially longer with minimum maintenance and upkeep required. Moreover, the design of the present invention is not subject to sensitive malfunctions in circuitry, as is also the case of prior sampler devices. Consequently, the present invention represents a simple, inexpensive, yet very efficient and long term technique of maintaining a constant volume flow control within an aerosol sampling device.

It will be understood that the present invention may be embodied in other specific forms without departing from the spirit or central characteristics thereof. The present examples and embodiments, therefore, are to be considered in all respects as merely illustrative and not restrictive, and the invention is not to be limited to the details provided herein but may be modified within the scope of the appended claims.

I claim:

1. A volume flow control device for an aerosol sampler that has an air inlet through which ambient air can be drawn into said sampler, a particle fractionator for separating and retaining aerosol particles above a predetermined cut size and an air outlet for passing the air flow and aerosol particles under the cut size out of the fractionator, comprising:

particulate filter means for catching and retaining particulate matter flowing in said aerosol out of the fractionator including duct means connected to said air outlet and to said filter means for conducting the aerosol from the fractionator to said filter means, critical flow venturi means for maintaining a predetermined volumetric flow rate $Q_o$ of aerosol through said sampler said venturi means being connected to said filter means and said venturi means having a converging inlet portion, a throat portion with an internal surface in the form of a figure of revolution defined by an arc of a circle rotating about the longitudinal axis of the venturi means with a minimum throat cross-section having a diameter $d_m$ defined by the ratio $10 \leq (Q_o/d_m) \leq 100$ where $Q_o$ is in c.f.m. and $d_m$ is in inches, and a diverging outlet portion; and blower means connected to said venturi means for creating a vacuum downstream of said venturi means sufficient to maintain said venturi means in choked condition at $Q_o$.

2. The flow control device as claimed in claim 1, wherein said vacuum comprises approximately 10 to 30 inches of water.

3. The flow control device as claimed in claim 1, wherein the arc of curvature of said throat portion has a radius of approximately 10 to 20 times the minimum diameter dm of said throat portion.

4. The flow control device as claimed in claim 3, wherein said throat portion has a minimum diameter in the range of about 0.4 to 0.5 inches and an arc of curvature with a radius of about 5 inches, and wherein the total angle of divergence of said diverging portion is about 10°.

5. The flow control device as claimed in claim 1, wherein the ratio of the axial length $L_t$ of said throat portion to the minimum diameter $d_m$ of said throat portion is in the range of about 1 to 8.

6. The flow control device as claimed in claim 5, wherein said ratio of $L_t$ to $d_m$ is about 5.

7. The flow control device as claimed in claim 1, wherein the total angle of divergence of said diverging portion is no greater than about 10°.

8. The flow control device as claimed in claim 1, wherein said filter means has a substantially rectangular shape and said venturi means includes an elongated converging contraction portion that has a substantially rectangular transverse cross-section adjacent said filter means and that has a gradual converging transition in cross-section to circular leading into a throat portion of said venturi means that is substantially circular in cross-section.

9. An aerosol sampling device, comprising:
air inlet means,
means for removing larger particulates from an inlet aerosol flow that is drawn into said air inlet means;
means for filtering and capturing the finer aerosol particulates from the aerosol flow, including a removable filter member having a substantially rectangular cross-section;
means for drawing said aerosol into said device and through said filter means; and
critical flow venturi means adapted for maintaining a predetermined volumetric flow rate $Q_o$ of aerosol through said filter means independent of particulate accumulation on said filter means by being in choked condition at $Q_o$ said aerosol drawing means being adapted to create a vacuum downstream of said venturi means and wherein said venturi means has a substantially rectangular cross-section adjacent the filter member and converges to substantially circular cross-section at a constricted throat and then diverges beyond said throat.

10. The aerosol sampling device of claim 9, wherein said venturi means is disposed between said filter means and said aerosol drawing means.

11. The sampling device as claimed in claim 10, wherein said larger particulate removal means separates from the particle laden flow particulates having a size greater than about 10 microns when $Q_o$ is maintained, and wherein said filter means captures the aerosol particulates of about 10 microns in size and smaller.

12. The sampling device as claimed in claim 9, wherein said aerosol drawing means comprises blower means adapted to create a vacuum sufficient to maintain said venturi means at its critical flow rate $Q_o$ condition and wherein the minimum diameter $d_m$ of the throat is defined by the ratio in the range of $10 \leq (Q_o/d_m) \leq 100$ where $Q_o$ is measured in cubic feet per minute and $d_m$ is measured in inches.

13. The sampling device as claimed in claim 12, wherein said critical flow rate $Q_o$ is predetermined to provide a substantially constant volume flow of aerosol through said filter means in the range of about 0.5 to 50 c.f.m.

14. The sampling device as claimed in claim 9, wherein the internal surface of said throat portion has a longitudinal radius of curvature approximately 10 to 20 times the minimum diameter of said throat portion, wherein the ratio of the length of said throat portion to the minimum diameter of said throat portion is approximately 1 to 8, and wherein the angle of divergence of said diverging outlet portion is approximately 10°.

15. A method for controlling an aerosol flow of air through an aerosol sampling device having a particulate filter member, said method comprising the steps of:
drawing said aerosol at a predetermined volumetric rate into said sampling device and through said filter member;
directing the filtered air through a critical flow venturi that contracts the air flow from a cross-section at its entrance to a cross-section at its throat of less than one-fiftieth said entrance cross-section and goes into choked condition at said predetermined volumetric rate; and
creating a vacuum downstream of said venturi sufficient to maintain the volumetric flow of filtered air through said venturi at the predetermined volumetric rate.

16. The method as claimed in claim 15, including the step of maintaining predetermined volumetric flow through said filter member in the range of 0.5 to 50 c.f.m.

17. The method as claimed in claim 15, including the step of maintaining said vacuum in the range of 10 to 30 inches of water.

18. The method as claimed in claim 15, including the steps of converging said filtered air in said venturi to a narrowed throat portion having a predetermined longitudinal radius of curvature drawn along the length of said throat portion a distance approximately 1 to 8 times the minimum diameter of said throat portion, and then diverging said air outwardly from said throat portion at an angle of divergence no greater than about 5° off axial center to preclude flow separation along the surface downstream of said throat portion to thereby create and maintain a stable shock wave within said throat portion at said predetermined volumetric flow rate and to recover energy required to establish the shock wave.

19. A method of sampling suspended particulates in an aerosol, comprising the steps of:
directing said aerosol through a sampler inlet that has the capability of fractionating and separating the larger particulates above a predetermined cut point size from similar particulates below the cut point size when the aerosol is drawn through the sampler inlet at a predetermined design volumetric flow rate Qo;

removing the larger particulates from said aerosol in said sampler inlet and allowing the remaining smaller particulates to flow through and out of said sampler inlet with the aerosol air flow;

directing all of the aerosol and smaller particulates from said sampler inlet through a filtering media and filtering the smaller particulates from said aerosol with the filtering media;

directing all of the aerosol air flow downstream of said filtering media through a critical flow venturi that is profiled and sized to be in choked condition at about said volumetric flow rate Qo, including the steps of directing said aerosol air flow from said filtering media into a converging contraction section of the venturi with interior sidewalls that converge toward the longitudinal axis of the venturi at an angle in the range of 10° to 20° and decreases in cross-sectional area to a throat portion that is no greater than one-fiftieth the cross-sectional area of the entrance to the venturi, directing the air flow through the throat section and into a diffuser section that has interior sidewalls that diverge from said throat section outwardly at an angle from the longitudinal axis of the venturi no greater than about 5°; and creating and maintaining a vacuum downstream of the diffuser section of said venturi sufficient to maintain the volumetric flow of air through said venturi at the volumetric flow rate $Q_o$, thereby maintaining a predetermined constant volumetric flow rate $Q_o$ of aerosol through the inlet sampler and filtering media regardless of particulate accumulation therein and regardless of ambient air temperature and stagnation pressure conditions both upstream and downstream of the filtering media.

20. In ambient aerosol sampler apparatus including a fractionator inlet for drawing in a particle laden ambient aerosol and for separating and retaining aerosol particles larger than a predetermined cut point size and passing through aerosol particles smaller than the predetermined cut point size, a rectangular filter element downstream from the fractionator inlet for catching and retaining for analysis the aerosol particles smaller than the cut point size, and a duct connecting said inlet to said filter, the improvement comprising:

volumetric flow control means for creating and maintaining a constant volumetric flow of air through said inlet and filter, said volumetric flow control means comprising a rectangular filter mount housing of a size and shape corresponding to the size and shape of said filter, critical flow venturi means downstream of said filter for maintaining the volumetric flow rate of the aerosol at the constant predetermined rate required for the correct operation of the fractionator inlet, and blower means connected to said venturi means for drawing said aerosol through said fractionator inlet, through said filter, and through said venturi means, said venturi means comprising a rectangular top section that includes at its top said filter mount housing, a converging section extending axially downwardly and inwardly to a throat section of circular cross-section sized to cause a choked flow condition at said predetermined volumetric flow rate, said converging section being gradually and smoothly transformed from a rectangular cross-section adjacent the filter mount housing to a circular cross-section adjacent the throat, and a diverging section of circular cross-section extending axially downwardly from said throat section, said diverging section diverging downwardly and outwardly in a frustoconical shape to said blower means.

21. The improvement of claim 20, wherein said converging portion adjacent said throat portion is approximately frustoconical in shape with its interior sidewalls converging toward the longitudinal axis of said throat portion at an angle in the range of about 10° to 20°, said throat portion has an hour glass shaped inner surface with a minimum diameter $d_m$ defined in inches by the range of $10 \leq (Q_o/d_m) \leq 100$ where Qo is the design flow rate in c.f.m. of the aerosol fractionator inlet, the radius of curvature of said throat inner surface being in the range of about 5 to 20 times $d_m$, the axial length of the throat Lt being defined by the ratio of $L_t/d_m$ in the range of about 1 to 8, and the interior walls of the frustoconical diverging section diverging from the longitudinal axis of said throat portion at an angle in a range no greater than about 5°, and wherein the inner surfaces of said converging section, said throat section, and said diverging section are smoothly blended together to avoid any abrupt transitions in the sidewalls.

22. Flow controller apparatus for an ambient aerosol sampler inlet that has an air intake for conducting ambient air into the sampler inlet and an air outlet for conducting air from the sampler inlet to a particle receptacle at which particles exiting the sampler inlet are collected for measuring, comprising:

critical flow venturi means connected to said air outlet for limiting the volumetric flow of air through said sampler inlet to a predetermined rate $Q_o$, said venturi means being connected to said air outlet in such a manner that all of the air flow through said sampler inlet is directed into said venturi means, and said venturi means being comprised of a converging contraction section merging into a constricted throat section of circular cross section that in turn merges into a diverging diffuser section, the minimum diameter $d_m$ in inches of said constricted throat portion being in the range of $10 \leq (Q_o/d_m) \leq 100$ such that said venturi has a choked flow condition at the throat portion when the volumetric air flow therethrough is $Q_o$ in c.f.m., and the entrance to said contraction section being at least twice as large in cross-sectional area as the exit of said diffuser section; and blower means connected to said venturi means for inducing sufficient volumetric flow through said venturi to maintain the choked condition at Qo.

23. The flow controller apparatus of claim 22, wherein the cross-sectional area of the entrance of the contraction section is more than fifty times the smallest cross-sectional area of throat portion, thereby having a contraction ratio of at least 50 to 1.

24. The flow controller apparatus of claim 23, wherein said contraction section is comprised of a funnel section converging down to an inlet portion, wherein said funnel section has an entrance with a rectangular cross-section and converges in shape and size from said rectangular funnel entrance to a said inlet portion, which inlet portion has an entrance with a circular cross-section and continues to converge in circular cross-section to said throat portion.

25. The flow controller apparatus of claim 24, wherein the cross-sectional area of the entrance to said inlet portion is at least fifty times the smallest cross-sectional area of the throat portion and the cross-sectional area of the entrance to said funnel section is at least two hundred times the smallest cross-sectional area of the throat.

26. The flow controller apparatus of claim 25, wherein said particle receptacle is a filter membrane positioned across the entrance to said funnel section.

27. Flow controller apparatus for an ambient aerosol sampler inlet that has an air intake for conducting ambient air into the sampler inlet and an air outlet for conducting air from the sampler inlet to a particle receptacle at which particles exiting the sampler inlet are collected for measuring, comprising:

critical flow venturi means connected to said outlet for limiting the volumetric flow of air through said sampler inlet to a predetermined rate $Q_o$, said venturi means being connected to said air outlet in such a manner that all of the air flow through said sampler inlet is directed into said venturi means, and said venturi means being comprised of a converging contraction section merging into a constricted throat portion of circular cross-section that in turn merges into a diverging diffuser section, the minimum diameter $d_m$ in inches of said constricted throat portion being in the range of $10 \leq (Q_o/d_m) \leq 100$ such that said venturi has a choked flow condition at the throat portion when the volumetric flow therethrough is $Q_o$ in c.f.m., and the cross-sectional area of the entrance to said contraction section being at least fifty times larger than the smallest cross-sectional area of the throat portion, thereby having a contraction ratio of at least 50 to 1; and blower means connected to said venturi means for inducing sufficient volumetric flow through said venturi to maintain the choked condition at $Q_o$.

28. The flow controller apparatus of claim 27, wherein said contraction section is comprised of a funnel section converging down to an inlet portion, wherein said funnel section has an entrance with a rectangular cross-section and converges in shape and size from said rectangular funnel entrance to a said inlet portion, which inlet portion has an entrance with a circular cross-section and continues to converge in circular cross-section to said throat portion.

29. The flow controller apparatus of claim 28, wherein the cross-sectional area of the entrance to said inlet portion is at least fifty times the smallest cross-sectional area of the throat portion and the cross-sectional area of the entrance to said funnel section is at least two hundred times the smallest cross-sectional area of the throat.

30. The flow controller apparatus of claim 29, wherein said particle receptacle is a filter membrane positioned across the entrance to said funnel section.

31. The flow controller apparatus of claim 29, wherein the entrance to said contraction section is at least twice as large in cross-sectional area as the exit of said diffuser section.

32. The flow controller apparatus of claim 27, wherein at least a portion of said contraction section is substantially frustoconical in shape with its interior sidewalls converging toward the longitudinal axis of said throat section at an angle in the range of about 10° to 20°, said throat section has an hour glass-shaped inner surface profile in the form of a figure of revolution defined by the arc of a circle rotated about the longitudinal axis of the throat section with the radius of curvature of the arc being in the range of about 5 to 20 times $d_m$.

33. The flow controller apparatus of claim 32, wherein said diffuser section is substantially frustoconical in shape, the interior walls of which diverge from the longitudinal axis of said throat section at an angle in the range of no greater than 5°.

34. The flow controller apparatus of claim 33, wherein the axial length $L_t$ of said throat section is defined by the ratio of $L_t/d_m$ in the range of about 1 to 8.

35. Flow controller apparatus for an ambient aerosol sampler, comprising:

critical flow venturi means connected to said sampler for limiting the volumetric flow of air through said sampler at a predetermined rate $Q_o$, said venturi means being comprised of a converging contraction section merging into a constricted throat section of circular cross-section that has a minimum diameter $d_m$, which throat section in turn merges into a diverging diffuser section, the minimum diameter $d_m$ in inches being in the range of $10 \leq (Q_o/d_m) \leq 100$ such that said venturi has a choked flow condition at the throat portion when the volumetric airflow therethrough is $Q_o$ in c.f.m.

36. Flow controller apparatus for an ambient aerosol sampler, comprising:

critical flow venturi means connected to said sampler for limiting the volumetric flow of air through said sampler at a predetermined rate, said venturi means having a rectangular entrance, a converging section that extends from said rectangular entrance axially downwardly and inwardly to a throat section of circular cross-section sized to cause a choked flow condition at said predetermined volumetric flow rate, said converging section being gradually and smoothly transformed from a substantially rectangular cross-section at the entrance to a substantially circular cross-section adjacent the throat.

37. Flow controller apparatus for an ambient aerosol sampler, comprising:

critical flow venturi means connected to said sampler for limiting the volumetric flow of air through said sampler at a predetermined rate, said critical flow venturi means including a constricted elongated throat portion having a longitudinal axis, a length $L_t$ and a minimum diameter $d_m$, a converging portion leading longitudinally into said throat portion, and a diverging portion leading longitudinally away from said throat portion, said converging portion having interior sidewalls converging toward the longitudinal axis of the throat portion at an angle in the range of 10° to 20°, said throat portion having an hour glass-shaped inner surface profile in the form of a figure of revolution substantially defined by an arc of a circle rotated about the longitudinal axis of the throat portion with the radius of curvature of the arc in the range of about 5 to 20 times $d_m$ and the ratio of $L_t/d_m$ is in the range of about 1 to 8, and said diverging portion diverging from the throat portion at no more than 5° from the longitudinal axis.

38. Flow controller apparatus for an ambient aerosol sampler comprising:

critical flow venturi means connected to said sampler for limiting the volumetric flow of air through said sampler at a predetermined rate, said critical flow venturi means including a converging contraction section merging into a constricted throat section of circular cross-section that in turn merges into a diverging diffuser section, wherein the cross-sectional area of the entrance of said contraction section being at least fifty times larger than the smallest cross-sectional area of the throat section, thereby having a contraction ratio of at least 50 to 1.

* * * * *